US007098243B2

(12) United States Patent
Sas et al.

(10) Patent No.: US 7,098,243 B2
(45) Date of Patent: Aug. 29, 2006

(54) BICYCLIC CARBOHYDRATES AS ANTIVIRAL BIOACTIVES FOR THE TREATMENT OF INFECTIONS CAUSED BY THE ALPHAHERPESVIRINAE HSV-1 AND HSV-2

(75) Inventors: Benedikt Sas, Stekene (BE); Johan Van hemel, Antwerp (BE); Jan Vandenkerckhove, Zichem (BE); Eric Peys, Balen (BE); Johan Van Der Eycken, Ninove (BE); Steven Van Hoof, Genk (BE)

(73) Assignee: Kemin Pharma Europe B.V.B.A., Des Moines, IA (US)

( * ) Notice: Subject to any disclaimer, the term of this patent is extended or adjusted under 35 U.S.C. 154(b) by 25 days.

(21) Appl. No.: 10/663,962

(22) Filed: Sep. 16, 2003

(65) Prior Publication Data

US 2005/0059612 A1 Mar. 17, 2005

(51) Int. Cl.
*A61K 31/70* (2006.01)
*C07D 493/02* (2006.01)

(52) U.S. Cl. ........................ 514/456; 549/364; 549/365

(58) Field of Classification Search ................ 549/364, 549/365; 514/456

See application file for complete search history.

(56) References Cited

U.S. PATENT DOCUMENTS 5,753,141 A 5/1998 Siemensmeyer et al.

FOREIGN PATENT DOCUMENTS

WO WO 03/082846 A1 10/2003
WO WO 04/014929 A1 2/2004

OTHER PUBLICATIONS

Exhibit I, search result.*

Akanitapichat et al. "1,3-dihydroxyacridone . . . " CA 133:26483 (2000).*

Database CAPLUS on STN, AN 2001:544756. Espinola et al. "Synthetic Flux-Promoting Polyether Modstl: Cation Flux Dependence on Polyoxyethylene Chain Length", Isreal Journal of Chemistry. 2000, vol. 40, Issue 3-4.

* cited by examiner

*Primary Examiner*—Celia Chang
(74) *Attorney, Agent, or Firm*—Kent A. Herink; Daniel A. Rosenberg; Emily E. Harris

(57) ABSTRACT

Novel bicyclic carbohydrate compounds are effective for the prophylaxis and treatment of diseases caused by infections of the alphaherpesvirinae HSV-1 and HSV-2. The invention includes the compound

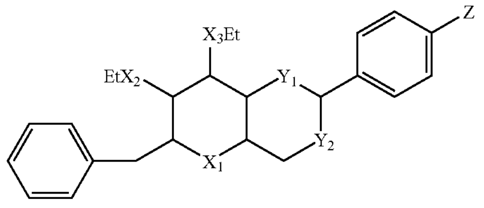

wherein $X_1$, $X_2$, and $X_3$ are selected from the group consisting of O, N, and S; wherein $Y_1$ and $Y_2$ are selected from the group consisting of O, N, and S; and wherein Z is selected from the group consisting of F, Cl, and Br, as well as analogs, prodrugs and pharmaceutically acceptable salts thereof, together with pharmaceutical compositions for the prophylaxis and treatment of diseases caused by infections of alphaherpesvirinae.

7 Claims, 5 Drawing Sheets

2,3,4,6-tetra-O-benzyl
-D-glucose 3.1

3.2

3.3

3.4

Compound A1

BICYCLIC CARBOHYDRATES AS ANTIVIRAL BIOACTIVES FOR THE TREATMENT OF INFECTIONS CAUSED BY THE ALPHAHERPESVIRINAE HSV-1 AND HSV-2

BACKGROUND OF THE INVENTION

The invention relates generally to compounds active against viral diseases and, more specifically, to bicyclic carbohydrates that are active against infections caused by the alphaherpesvirinae HSV-1 and HSV-2.

Infections by herpes viruses are among the most common and easily transmitted viral conditions. Numerous distinct viruses have been identified and the treatment by chemotherapeutic agents of diseases caused by some of these, such as HSV-1, HSV-2 and VZV (varicella-zoster virus), has produced substantial clinical benefit.

The genomic linear double-stranded DNA of the herpes viruses codes for about 100 polypeptides. While the functions of most of the encoded proteins are poorly understood, a number of them are well characterized and include enzymes which provide excellent targets, or have vital implications, for chemotherapy. These include a DNA polymerase essential for replication, a protease and, significantly for HSV-1, HSV-2 and VZV, a thymidine kinase. Anti-herpes virus agents often show a broad spectrum of activity across the family, a consequence of structural similarities between the functional proteins, although the presence or absence of the thymidine kinase is usually a key factor in selectivity.

Herpes simplex viruses type 1 and 2 cause a broad spectrum of diseases in humans including labial and genital herpes (R. J. Whitley. Herpes simplex viruses. in Fields virology (eds. B. N. Fields, D. M. Knipe and P. M. Howley) 2297–2342 (Raven, New York, 1995)). The diseases all could be caused by either virus, though HSV-1 primarily affects the upper part of the body whereas HSV-2 is more commonly associated with genital infections. Although HSV diseases are not usually life threatening, recurrences can dramatically affect the quality of life of afflicted individuals. Nucleoside analogs such as acyclovir, valacyclovir, famciclovir and penciclovir have been approved as the drugs of choice for the treatment of HSV infections (C. M. Perry, D. Faulds. Valacyclovir. A review of its antiviral activity, pharmacokinetic properties and therapeutic efficacy in herpesvirus infections. *Drugs* 52, 754–772 (1996)).

These drugs inhibit the viral DNA polymerase after activation by the viral thymidine kinase (R. A. Vere Hodge. Famciclovir and penciclovir. The mode of action of famciclovir including its conversion to penciclovir. *Antiviral Chem. Chemother.* 4, 67–84 (1993); J. E. Reardon and T. Spector. Acyclovir: mechanism of action and potentiation by ribonucleotide reductase inhibitors. in *Advances in Pharmacology* (ed. T. Augusta) 1–27 (Academic, New York, 1991)).

Acyclovir, as a treatment for HSV infections, was the first example of a genuinely selective antiviral agent. Via some interactions acyclovir slows down the DNA-replication. However, it is only the triphosphate of acyclovir that interacts with the virus-specific DNA polymerase (P. A. Furman, M. H. StClair, J. A. Fyfe, J. L. Rideout, P. M. Keller, G. B. Ellion. *J. Virol.* 32, 72 (1979)). Acyclovir triphosphate (ACV-TP) itself is formed via its mono- and diphoshate intermediates. Already in the first step, the conversion of ACV in its monophosphate form, the first point of selectivity can be found. This step is carried out by an enzyme coded by the virus, viral coded thymidine kinase (TK), which can only be found in virally infected cells. Nevertheless there are cellular counterparts, cellular thymidine kinases, but they show much higher substrate specificity. The viral enzyme is less specific and will recognize a larger diversity of nucleosides as substrate. This is why only in the viral infected cell acyclovir is converted by TK to its monophosphate, which is converted into the triphosphate by cellular enzymes. This is the first aspect of the selectivity of acyclovir: the triphosphate is only formed in infected cells. The obtained ACV-TP then acts as an inhibitor of DNA-polymerase. This is the second step in the selectivity process, since ACV-TP inhibits viral coded DNA polymerase stronger than that in healthy cells. As soon as ACV-TP is incorporated in the growing DNA-chain, it will act through the absence of a 3-OH group as a chain terminator (the same principle as AZT). Additionally the viral DNA polymerase is irreversibly bound to the ACV nucleotide it attached to the DNA chain. In this way the growth of the viral DNA chain as well as the availability of the viral DNA polymerase is diminished, which hampers viral replication severely.

Clinical isolates and, especially, laboratory mutant strains can be resistant to acyclovir and other nucleosides. Many of these strains have deleted or altered the thymidine kinase, which makes them unable to phosphorylate nucleosides. TK function is not vital to the survival of HSV, though it may be able to increase replication rates. In vitro methods have produced acyclovir resistant phenotypes, which have an alteration in the function of the DNA polymerase. These are potentially a bigger problem, but so far appear to be of little clinical significance. When acyclovir resistance causes significant problems, foscarnet is used; however, mutants where acyclovir resistance is due to altered DNA polymerase function can also be resistant to foscarnet and phosphonate isosters of nucleoside monophosphates. Nucleoside-resistant HSV infections are increasingly encountered in immunocompromised individuals (D. W. Kimberlin et al. Antiviral resistance in clinical practice. *Antiviral Res.* 26, 423–438 (1995)). Therefore, pharmacologically distinct anti-HSV agents with significantly improved therapeutic efficacy are developed, such as HSV helicase-primase inhibitors (J. J. Crute et al. Herpes simplex virus helicase-primase inhibitors are active in animal models of human disease. *Nature Med.* 8, 386–391 (2002)) or inhibitors that block protein-protein interactions (N. Moss et al. Peptidomimetic inhibitors of herpes simplex virus ribonucleotide reductase with improved in vivo antiviral activity. *J. Med. Chem.* 39, 4173–4180 (1996)).

Alternative compounds with activity against herpes viruses such as HSV-1 and HSV-2 are needed.

SUMMARY OF THE INVENTION

The invention consists of the novel bicyclic carbohydrate the structure of which is illustrated in FIG. 1 and which is identified herein as Formula A. Compounds of Formula A have activity against infections caused by the alphaherpesvirinae HSV-1 and HSV-2.

DETAILED DESCRIPTION OF A PREFERRED EMBODIMENT

Figure 1:
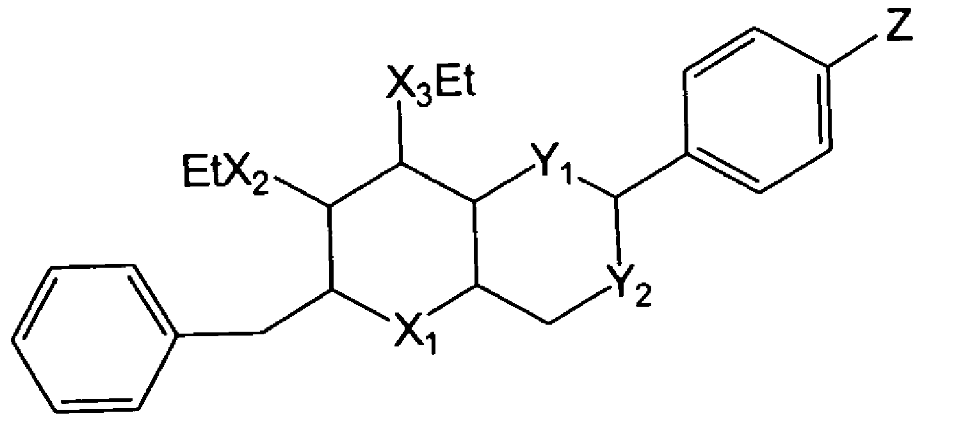
FIG. 1 is a chemical structure of the bicyclic carbohydrates of the present invention and designated Formula A.
Figure 2:
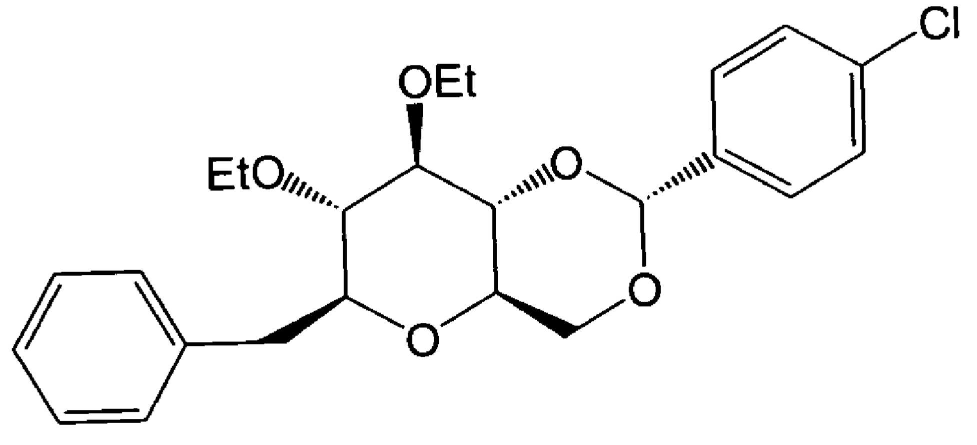
FIG. 2 is a chemical structure of preferred embodiment of the present invention and designated Compound A1.
Figure 3:
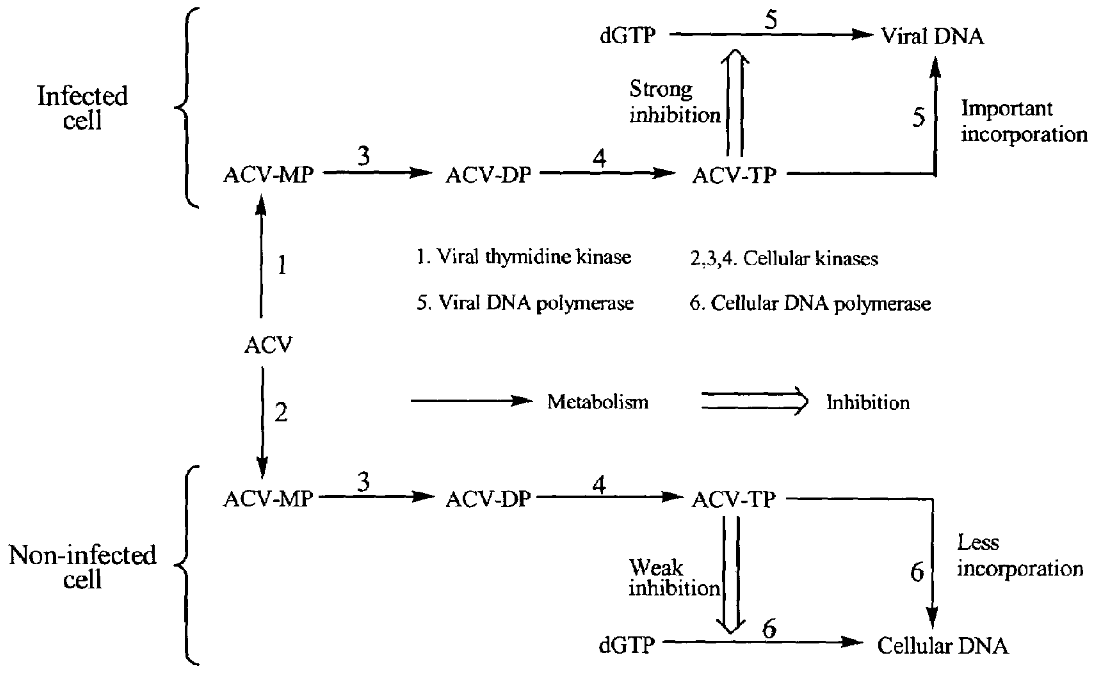
FIG. 3 is a diagrammatic representation of the activity of acyclovir in cells that are non-infected and cells that are infected with herpes virus.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, acetate ascorbate, benzoate, citrate, etoglutarate, glycerophosphate, malonate, methanesulfonate, succinate, and tartarate. Suitable inorganic salts may also be formed, including bicarbonate, carbonate, hydrochloride, nitrate, and sulfate, salts.

Compounds of the present invention can conveniently be administered in a pharmaceutical composition containing the compound in combination with a suitable excipient, the composition being useful in combating viral infections. Depending on whether the preparation is used to treat internal or external viral infections, the compounds and compositions of the present invention can be administered parenterally, topically, intravaginally, orally, or rectally.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity. Methods for the extrapolation of effective dosages to humans are known to the art.

The compound is conveniently administered in unit dosage form; for example, containing 0.1 to 2000 mg, conveniently 100 to 1000 mg, most conveniently, 250 to 750 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 30 mg/kg, preferably 1 to 10 mg/kg of mammal body weight, and can be used in man in a unit dosage form, administered one to four times daily.

For parenteral administration or for administration as drops, as for eye infections, the compounds are presented in aqueous solution in a concentration of from about 0.1 to about 20%, more preferably about 1 to about 5%. The solution may contain other ingredients, such as emulsifiers, antioxidants or buffers.

The exact regimen for administration of the compound and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Compounds of Formula A and pharmaceutically acceptable salts thereof are useful as antiviral agents. Thus, they are useful to combat viral infections in animals, including man. The compounds are generally active against herpes viruses, and are particularly useful against the herpes simplex virus types 1 and 2 (HSV-1 and 2).

Methods and Materials

The bicyclic carbohydrates are synthesized as described below.

Synthesis of Compound A1

Figure 4:
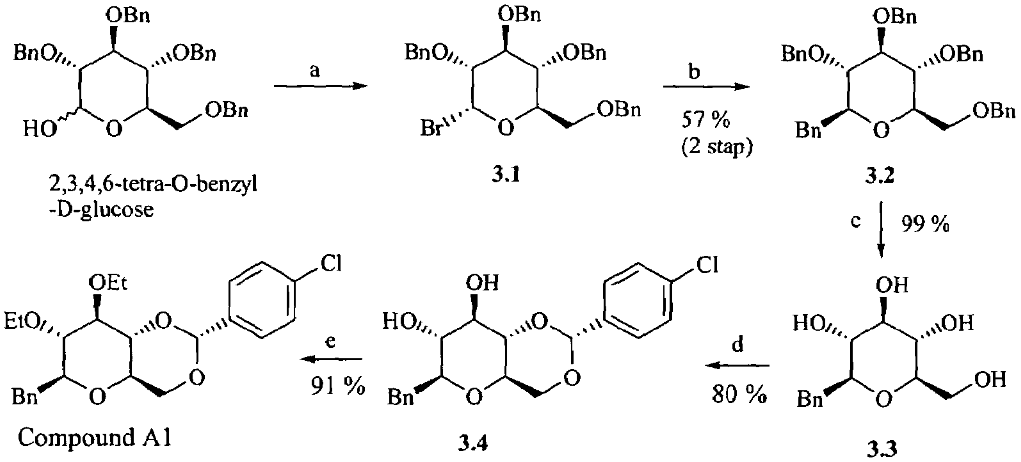
FIG. 4 is a diagram illustrating the scheme for synthesizing Compound A1.
Figure 5:
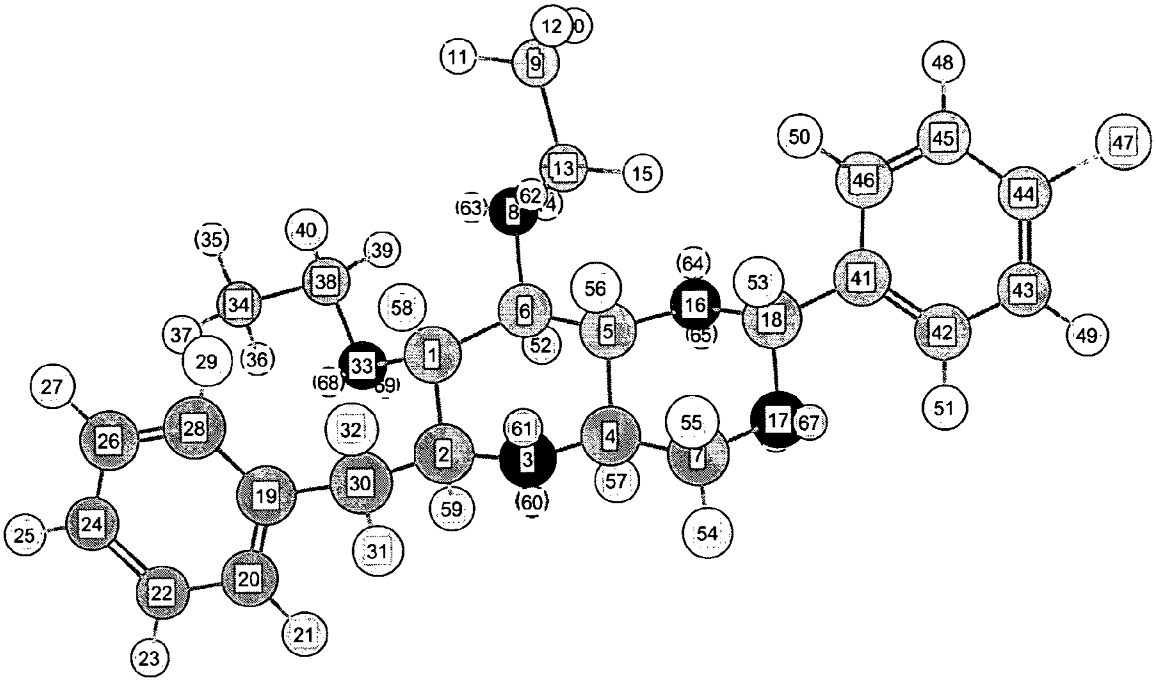
FIG. 5 is a three-dimensional representation of Compound A1.

The scheme for synthesizing Compound A1 is illustrated in FIG. 4.

Synthesis of Compound 3.1

To a solution of 2,3,4,6-tetra-O-benzyl-D-glucose (10.0 g, 18.5 mmol) in dry $CH_2Cl_2$ (125 ml) and DMF (6.25 ml) was added at room temperature a solution of oxalylbromide (2.5 ml of a 10M sol in $CH_2Cl_2$, 1.35 eq). The addition caused a violent formation of a gas. The reaction mixture was stirred at room temperature under argon-atmosphere for 60 min. Subsequently the reaction mixture was poured out into ice water (125 ml). After separation of layers, the organic layer was washed with ice water (2×125 ml). Drying on $MgSO_4$, and concentrating under reduced pressure yielded a yellow oil that was used in the next reaction step without further purification.

Formula: $C_{34}H_{35}BrO_5$

Molecular weight: 603.55

$R_f$: 0.53 (cyclohexane/ethyl acetate 85:15)

$^1$H-NMR (500 MHz, $CDCl_3$): 7.37 (3H, m), 7.33 (5H, m), 7.31 (5H, m), 7.28 (5H, m), 7.15 (2H, m), 6.43 (1H, d, J=3.7 Hz), 4.98 (1H, d, J=5.0 Hz), 4.83 (2H, dd, app. t, J=10.9 Hz), 4.58 (1H, d, J=12.1 Hz), 4.50 (1H, d, J=10.7 Hz), 4.46 (2H, d, J=12.1 Hz), 4.06 (1H, m), 4.03 (1H, dd, app. t, J=9.2 Hz), 3.80 (1H, m), 3.78 (1H, m), 3.76 (1H, d, J=4.6 Hz), 3.65 (1H, dd, J=11.0, 2.0 Hz), 3.54 (1H, dd, J=9.2, 3.7 Hz)

Synthesis of Compound 3.2

To a solution of Compound 3.1 (18.5 mmol theoretical) in dry $Et_2O$ (250 ml), cooled to 0° C., was slowly added benzylmagnesium chloride (150 ml of 1M-opl. in $Et_2O$, 8 eq). The reaction mixture was stirred at 0° C. for 1 hour, after which the mixture was allowed to reach room temperature. After stirring overnight at room temperature, the reaction mixture was poured out into $H_2O$ (500 ml) and AcOH (100 ml), followed by separation of layers. The organic layer was washed with 3×500 ml sat. $NaHCO_3$-sol. and 250 ml sat. NaCl-sol. Drying on $MgSO_4$, and concentrating under reduced pressure gave the crude product, which was purified by column chromatography (60–230 mesh silica, gradient: toluene:cyclohexane 8:2, toluene, cyclohexane:ethyl acetate 9: 1). This yielded 6.47 g of Compound 3.2 (57% over 2 steps) as a colorless oil.

Formula: $C_{41}H_{42}O_5$

Molecular weight: 614.78

$R_f$: 0.15 (cyclohexane/diethylether 9:1)

$[\alpha]_D^{20}$=+85.3°; $[\alpha]_{365}^{20}$=+88.1° (c=0.60 in chloroform)

IR(KBr): ($cm^{-1}$) 2862, 2360, 1604, 1496, 1454, 1360, 1209, 1085, 1028, 735, 697, 668

ES-MS: 632=$[M+NH_4]+$ $^1$H-NMR (500 MHz, $CDCl_3$): δ 7.36 (5H, m), 7.34 (5H, m), 7.31 (5H, m), 7.29 (5H, m), 7.26 (2H, m), 7.22 (3H, m), 4.96 (1H, d, J=11.0 Hz), 4.95 (1H, d, J=11.0 Hz), 4.91 (1H, d, J=11.0 Hz), 4.84 (1H, d, J=10.8 Hz), 4.69 (1H, d, J=11.0 Hz), 4.62 (1H, d, J=10.8 Hz), 4.59 (1H, d, J=12.2 Hz), 4.52

(1H, d, J=12.2 Hz), 3.74 (1H, dd, app. t, J=9.0 Hz), 3.69 (1H, m), 3.68 (1H, m), 3.66 (1H, dd, app. t, J=9.3 Hz), 3.52 (1H, ddd, J=18.3, 9.2, 2.3 Hz), 3.37 (1H, dd, app. t, J=9.0 Hz), 3.36 (1H, m), 3.17 (1H, dd, J=14.3, 2.0 Hz), 2.75 (1H, dd, J=14.3, 8.8 Hz) APT-NMR (125 MHz, $CDCl_3$): δ 138.9 (C), 138.7 (C), 138.5 (C), 138.3 (C), 138.2 (C), 129.7 (CH), 128.6 (CH), 128.6 (CH), 128.5 (CH), 128.4 (CH), 128.2 (CH), 128.0 (CH), 127.9 (CH), 127.8 (CH), 127.7 (CH), 127.6 (CH), 126.2 (CH), 87.5 (CH), 81.8 (CH), 80.1 (CH), 79.0 (CH), 78.7 (CH), 75.7 ($CH_2$), 75.2 ($CH_2$), 75.1 ($CH_2$), 73.5 ($CH_2$), 69.0 ($CH_2$), 38.0 ($CH_2$)

Synthesis of Compound 3.3

To a solution of Compound 3.2 (6.0 g, 9.76 mmol) in absolute EtOH (240 ml) was added at room temperature Pd on carbon (600 mg, 10 mol %). The reaction mixture was shaken at room temperature under 4 atm $H_2$-gas in a Parr-apparatus for 5 hours. Filtration over celite and concentration of the filtrate under reduced pressure gave 2.62 g residue as a white-yellow foam. Purification of the residue by column chromatography (60–230 mesh, $CH_2Cl_2$:MeOH 9:1) yielded 2.46 g of Compound 3.3 as a white foam (99%).

Formula: $C_{13}H_{18}O_5$

Molecular weight: 254.28

$R_f$: 0.14 (dichloromethane/methanol 9:1)

IR(KBr): ($cm^{-1}$) 3381, 2922, 2360, 2341, 1641, 1603, 1496, 1454, 1379, 1308, 1226, 1079, 1031, 897, 754, 701, 668

ES-MS: 272=$[254+NH_4]^+$ $^1$H-NMR (500 MHz, $CDCl_3$): δ 7.29 (2H, d, J=7.0 Hz), 7.22 (2H, dd, app. t, J=7.3 Hz), 7.14 (1H, m), 3.75 (1H, dd, J=11.9, 2.4 Hz), 3.60 (1H, dd, J=11.8, 5.4 Hz), 3.35 (1H, m), 3.32 (1H, m), 3.25 (1H, dd, app. t, J=9.4 Hz), 3.15 (1H, m), 3.12 (1H, m), 3.09 (1H, dd, app. t, J=9.3 Hz), 2.69 (1H, dd, J=14.5, 8.5 Hz)

APT-NMR (125 MHz, $CD_3OD$): δ 139.1 (C), 129.4 (CH), 127.6 (CH), 125.6 (CH), 80.4 (CH), 80.1 (CH), 78.6 (CH), 73.7 (CH), 70.6 (CH), 61.6 ($CH_2$), 37.4 ($CH_2$)

Synthesis of Compound 3.4

To a solution of Compound 3.3 (500 mg, 1.97 mmol) and p-chlorobenzaldehyde (1.38 g, 5 eq) in acetonitrile (12 ml), were added anhydrous copper(II)sulfate (942 mg, 3 eq) and CSA (46 mg, 0.1 eq). The reaction mixture was heated to reflux-temperature, and stirred as such overnight under argon-atmosphere. After TLC-analysis 2 eq. p-chlorobenzaldehyde and 0.1 eq CSA were added. After 4 hours the reaction mixture was poured out into $H_2O$ (100 ml), followed by extraction with $CH_2Cl_2$ (3×100 ml). The combined organic layers were washed with sat. NaCl-opl. (150 ml) and dried on $MgSO_4$. Filtration and concentration under reduced pressure gave a yellow-brown solid residue. Purification by column chromatography (60–230 mesh silica, $CH_2Cl_2$:iPrOH 97:3) and a purification by HPLC ($CH_2Cl_2$:iPrOH 97:3) yielded 596 mg desired Compound 3.4 (80%) and 20 mg epimer 3.5 (3%).

Formula: $C_{20}H_{21}ClO_5$

Molecular weight: 376.83

$R^f$: 0.25 ($CH_2Cl_2$:iPrOH 97:3)

Melting point: 106–108° C.

$[\alpha]_D^{20}$=−33.4°; $[\alpha]_{365}^{20}$=−105.0° (c=1.02 in chloroform)

IR (KBr): ($cm^{-1}$) 3390 (br), 2921 (m), 2867 (m), 1497 (m), 1377 (m), 1121 (s), 1088 (s), (m), 1016 (s), 1006 (s), 974 (m), 819 (m), 700 (m)

EI-MS: (m/z) 57 (23), 91 (100), 105 (33), 141 (51), 163 (5), 179 (5), 213 (4), 236 (3), 285 (6), 376 (23) [$M^+$]

ES-MS: 377 [$M+H^+$], 399 [$M+Na^+$]

$^1$H-NMR (500 MHz, $CDCl_3$): δ 7.42 (2H, d, J=8.5 Hz), 7.35–7.33 (2H, m), 7.31–7.22 (5H, m), 5.47 (1H, s), 4.27 (1H, dd, J=10.4, 4.9 Hz), 3.74 (1H; dd; app t, J=8.8 Hz), 3.66 (1H, dd, app t, J=10.2 Hz), 3.58 (1H, ddd, J=9.2, 8.0, 2.7 Hz), 3.42 (1H, dd, app t, J=9.2 Hz), 3.38 (1H, dd, app t, J=9.7 Hz), 3.36 (1H, ddd, app dt, J=9.7, 4.9 Hz), 3.18 (1H, dd, J=14.4, 2.6 Hz), 2.80 (1H, dd, J=14.4, 8.0 Hz), 2.79 (1H, s), 2.59 (1H, d, J=2.7 Hz)

APT-NMR (125 MHz, $CDCl_3$): δ 137.9 (C), 135.6 (C), 135.2 (C), 129.8 (CH), 128.6 (CH), 128.2 (CH), 127.8 (CH), 126.4 (CH), 101.0 (CH), 81.1 (CH), 80.3 (CH), 75.4 (CH), 73.8 (CH), 70.1 (CH), 68.9 ($CH_2$), 37.9 ($CH_2$)

Side Product 3.5

3.5

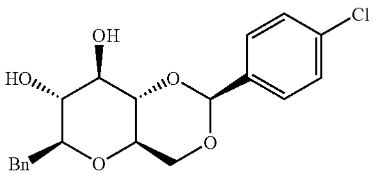

Formula: $C_{20}H_{21}ClO_5$

Molecular weight: 376.83

$R_f$: 0.25 ($CH_2Cl_2$:iPrOH 97:3)

Melting point: 184–186° C.

$[\alpha]_D^{20}$=+112.4°; $[\alpha]_{365}^{20}$+377.0° (c=0.46 in chloroform)

IR (KBr): ($cm^{-1}$) 3369 (br), 2911 (m), 1497 (m), 1371 (m), 1339 (m), 1110 (s), 1083 (s), 1028 (m), 1017 (s), 1001 (s), 979 (m), 946 (m), 827 (m), 810 (m), 739 (m), 696 (m)

EI-MS: (m/z) 57 (26), 91 (100), 105 (26), 141 (66), 175 (5), 179 (5), 213 (6), 243 (6), 285 (10), 376 (8) [$M^+$]

ES-MS: 377 [$M+H^+$], 399 [$M+Na^+$]

$^1$H-NMR (500 MHz, $CDCl_3$): δ 7,46 (2H, d, J=8.5 Hz), 7.37 (2H, d, J=8.5 Hz), 7.33–7.30 (2H, m), 7.26–7.23 (3H, m), 5.51 (1H, s), 4.35–4.33 (1H, m), 4.18 (1H, dd, J=10.5, 4.9 Hz), 3.99–3.96 (2H, m), 3.84 (1H, ddd, app dt, J=9.7, 4.9 Hz), 3.64 (1H, dd, app t, J=10.2 Hz), 3.53–3.47 (1H, m), 3.13 (1H, dd, J=14.9, 3.2 Hz), 2.98 (1H, dd, J=14.9, 11.6 Hz), 2.78 (1H, br s), 2.67 (1H, br s)

APT-NMR (125 MHz, $CDCl_3$): δ 138.5 (C), 135.6 (C), 135.2 (C), 129.0 (CH), 128.6 (CH), 128.6 (CH), 127.8 (CH), 126.4 (CH), 101.2 (CH), 82.0 (CH), 78.0 (CH), 72.4 (CH), 71.7 (CH), 69.2 ($CH_2$), 63.7 (CH)

Synthesis of Compound A1

To a solution of Compound 3.4 (100 mg, 0.265 mmol) in DMF (2.64 ml), cooled to 0° C., was added NaH (42 mg 60% dispersion, 4 eq). After 30 min stirring at 0° C., ethylbromide (99 μl, 5 eq) was added dropwise to the reaction mixture. Stirring was continued at 0° C. for 5 min, and at room temperature overnight. Subsequently the reaction mixture was poured out into $H_2O$ (25 ml), followed by extraction with $Et_2O$ (4x30 ml). The combined organic layers were washed with sat. NaCl-sol. (50 ml) and dried on $MgSO_4$. Filtration and concentration under reduced pressure gives 126 mg crude product as a white solid. Purification by column chromatography (230–400 mesh silica, pentane: ether 9:1, evaporation on silicagel was necessary) yields 105 mg Compound A1 (91%) as white crystals.

Formula: $C_{24}H_{29}CiO_5$

Molecular weight: 432.94

$R_f$: 0.23 (pentane:ether 9:1)

Melting point: 123–124° C.

$[\alpha]_D^{20}$=−40.5°; $[\alpha]_{365}^{20}$=−123.4° (c=1.00 in chloroform)

IR (KBr): ($cm^{-1}$) 2971 (m), 2899 (m), 2877 (m), 1371 (m), 1142 (m), 1109 (s), 1087 (s), 1033 (m), 1017 (m), 815 (m), 695 (m), 521 (m)

EI-MS: (m/z) 59 (37), 91 (100), 149 (43), 183 (14), 249 (5), 297 (14), 341 (4), 366 (3), 432 (2) [$M^+$]

$^1$H-NMR (500 MHz, $CDCl_3$): δ 7.40 (2H, d, J=8.5 Hz), 7.33 (2H, d, J=8.5 Hz), 7.30–7.21 (5H, m), 5.48 (1H, s), 4.23 (1H, dd, J=10.5, 5.0 Hz), 3.99 (1H, dq, J=9.1, 7.1 Hz), 3.92 (1H, dq, J=9.5, 7.1 Hz), 3.74 (1H, dq, J=9.5, 7.1 Hz), 3.68 (1H, dq, J=9.1, 7.1 Hz), 3.64 (1H, dd, app t, J=10.3 Hz), 3.54–3.45 (3H, m), 3.27 (1H, ddd, app dt, J=9.9, 5.0 Hz), 3.14 (1H, dd, J=14.3, 2.2 Hz), 3.08 (1H, dd, J=9.4, 8.4 Hz), 2.71 (1H, dd, J=14.3, 8.6)

APT-NMR (125 MHz, $CDCl_3$): δ 138.0 (C), 135.7 (C), 134.3 (C), 129.2 (CH), 128.9 (CH), 128.0 (CH), 127.7 (CH), 127.1 (CH), 125.8 (CH), 99.9 (CH), 82.9 (CH), 81.7 (CH), 81.3 (CH), 80.2 (CH), 69.7 (CH), 68.5 ($CH_2$), 68.4 ($CH_2$), 68.1 ($CH_2$), 37.8 ($CH_2$), 15.5 ($CH_3$), 15.4 ($CH_3$)

Bioactive Screening

The molecules were screened in vitro against a series of viruses such as West Nile virus, human cytomegalo virus (HCMV), herpes simplex virus type 1 (HSV-1), herpes simplex virus type 2 (HSV-2) and varicella zoster virus (VZV). The toxicity as well as the selectivity index (S.I.) was also determined.

For all viruses the $EC_{50}$ (effective compound concentration required to inhibit viral induced cytopathicity in HHF cells (HSV, HCMV and VZV) and Vero cells (West Nile virus) by 50%.) was determined.

For the determination of the antiviral activity against HSV-1 and HSV-2, the cytopathic effect inhibition assay (CPE) was used.

Low passage HFF cells are seeded into 96 well tissue culture plates 24 h prior to use at a cell concentration of $2.5\times10^5$ cells per ml in 0.1 ml of MEM supplemented with 10% FBS. The cells are then incubated for 24 h at 37° C. in a $CO_2$ incubator. After incubation, the medium is removed and 125 μl of experimental drug is added to the first row in triplicate wells, all other wells having 100 μl of media. The drug in the first row of wells is then diluted serially 1:5 throughout the remaining wells by transferring 25 μl using the BioMek Liquid Handling Machine. After dilution of drug, 100 μl of the appropriate virus concentration is added to each well, excluding cel control wells, which received 100 μl of MEM. For HSV-1 and HSV-2 the virus concentration added is 2500 PFU per well. The plates are then incubated at 37° C. in a $CO_2$ incubator for three days. After the incubation period, media is aspirated and the cells stained with a 0.1% crystal violet solution for four hours. The stain is then removed and the plates rinsed using tap water until all excess stain is removed. The plates are allowed to dry for 24 h and then read on a BioTek Plate Reader at 620 nm.

Based on the NCCLS (Reference Method for Broth Dilution Antifungal Susceptibility Testing of Yeast; Approved standard, NCCLS document M27-A; Reference Method for Dilution Antimicrobial Susceptibility Testing of Conidium-forming Filamentous Fungi; Proposed Standard, NCCLS document M38-P 18; Reference Method for Dilution Antimicrobial Susceptibility Tests for Bacteria that grow aerobically—Fourth Edition; Approved Standard, NCCLS document M7-A4) documents M7-A4, Vol. 17 No. 2, M27-A, Vol 17 No. 9 and M38-P, Vol 18 No. 13, a microdilution method was developed using a Bioscreen C Analyser (Labsystems, Finland), which is an automated reader-incubator. It measures growth continuously by vertical photometry (optical density), processes the data and provides a print-out of the results. For the bacteria the primary targets selected were *Staphylococcus aureus* ATCC29213, *Enterococcus faecalis* ATCC 29212, *Pseudomonas aeruginosa* ATCC 27853 and *Clostridium perfringens* ATCC 13124. *Candida albicans* ATCC 24433 and *Cryptococcus neoformans* ATCC 90112 were selected as yeast targets. The dermatophyte *Trichophyton mentagrophytes* ATCC 9533 and the invasive mould *Aspergillus fumigatus* ATCC 2895 were selected as moulds. All parameters necessary for optimal incubation can be programmed in the Biolink-software (Labsystems, Finland). Incubation for all bacterial screenings was 16 hours at 35° C. The incubation parameters for the screenings against *Candida* and *Cryptococcus* were respectively 24 and 48 hours at 35° C. The invasive fungus *Aspergillus fumigatus* was incubated for 3 days at 30° C. and the dermatophyte *T. mentagrophytes* was incubated for 5 days at 30° C. As growth media for the bacteria, cation adjusted Mueller-Hinton broth (Oxoid, Belgium) was used. A synthetic medium is recommended for fungal susceptibility tests; RPMI 1640, with glutamine, and without bicarbonate and with a pH indicator (Oxoid), supplemented with 1% glucose was selected for use. 25 μl of a 10-fold compound concentration is pipetted into each well. To each 25 μl test compound, 225 μl of growth media was added. As measurement tool for the antibacterial and anti-yeast screenings, the area under the growth curve automatically determined via the Biolink software is used. For the screenings against the pathogenic moulds, an endpoint OD-measurement was used. For internal quality control, reference antibiotics for each micro-organism are incorporated in the set-up of the tests.

Results and Discussion

In the anti-viral screenings, the activity of Compound A1 was determined against HSV-1, HSV-2, HCMV, VZV and West Nile virus (Table 1). Against the herpes viruses HSV-1 and HSV-2 a strong activity was observed. Acyclovir (ACV) and ganciclovir (GCV) are reference products used in the antiviral screening.

TABLE 1

Results of screenings against HSV-1, HSV-2, HCMV and VZV

| | Compound A1 | | | | GCV |
|---|---|---|---|---|---|
| Compound | $EC_{50}$[a] | $CC_{50}$ (μg/ml)[b] | S.I.[c] | ACV $EC_{50}$ (μg/ml) | $EC_{50}$ (μg/ml) |
| HSV-1 | 3 | >100 | >33.3 | 1.2 | — |
| HSV-2 | <0.03 | >100 | >3333 | 0.4 | — |
| HCMV | >20 | 71.0 | <3.5 | — | 0.8 |
| VZV | >100 | >100 | 0 | 0.39 | — |
| West Nile | >50 | 50 | 0 | — | — |

[a]50% Effective concentration or compound concentration required to inhibit viral-induced cytopathicity in HFF cell cultures by 50%.
[b]50% Cytotoxic Concentration or compound concentration required to reduce cell viability by 50%.
[c]Selectivity Index. S.I. = $CC_{50}/EC_{50}$ The antibacterial activity was screened against four reference bacteria; *S. aureus, E. coli, C. perfringens* and *P. aeruginosa* (Table 2). The compound did not show any significant antibacterial effect against the selected micro-organisms. The minimum inhibition concentration was above 25 μg/ml.

TABLE 2

| Results of the antibacterial screenings against Gram positive and Gram negative species | | | | |
|---|---|---|---|---|
| | MIC (μg/ml) | | | |
| Compound | *S. aureus* ATCC 29213 | *E. coli* ATCC 25922 | *C. perfringens* ATCC 13124 | *P. aeruginosa* ATCC 27853 |
| Compound A1 | >25 | >25 | >25 | >25 |

The antifungal activity was screened against four pathogenic yeasts and moulds (Table 3). None of the compounds showed any significant antifungal effect against the selected micro-organisms. The minimum inhibition concentration for both compounds was above 25 μg/ml.

TABLE 3

| Results of the screenings against pathogenic fungi | | | | |
|---|---|---|---|---|
| | MIC (μg/ml) | | | |
| Compound | *C. albicans* ATCC 24433 | *C. neoformans* ATCC 90112 | *T. mentagrophytes* ATCC 9533 | *A. fumigatus* ATCC 2895 |
| Compound A1 | >25 | >25 | >25 | >25 |

Compound A1 has high specificity for HSV. It is believed that Compound A1 works via a very tight key-lock interaction wherein the three-dimensional shape of the compound is critical to its activity. Relatively small changes on the structure that alter the three-dimensional spatial occupation of Compound A1 result in a decrease in activity. On the other hand, substitutions for atoms in the interior of the compound will less drastically alter the spatial occupation of the compound and so may be selected to affect the activity of Compound A1 without effectively removing all activity. Atoms on the exterior that have similar chemical properties may also be substituted to achieve an effect on activity without effectively destroying activity, for example by substituting other halides for the chlorine atom. Examples of compounds closely related to Compound A1 but having an altered three-dimensional spatial occupation are listed in Table 4 and their activity against HSV-1 and HSV-2 is provided.

TABLE 4

| Activities of compounds related to Compound A1 against HSV. | | |
|---|---|---|
| | $EC_{50}$ (μg/ml) | |
| Compound | HSV-1 | HSV-2 |
| 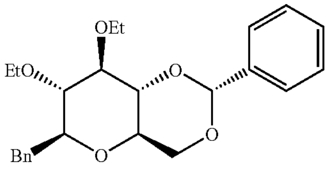 | >80 | >80 |
| 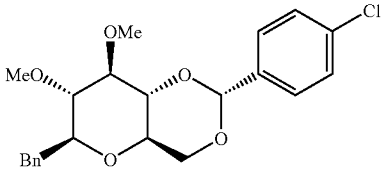 | >16 | >16 |
| 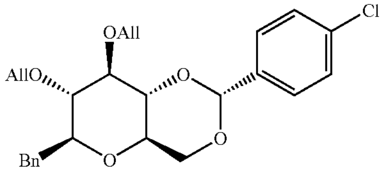 | >16 | >16 |

The data in Table 4 show that changes in size of the groups at wither position C2 or C3, causing a change in the spatial occupation of the compound in this region, resulted in a decreased activity. Further, changes in the C1 position, in the ring size of the sugar, and changes in the acetal part all resulted in a decreased activity. Based on these results, it can be concluded that very specific three-dimensional spatial occupations, specific physicochemical and specific electrochemical properties are required for the activity of these compounds.

Table 4 clearly show that if the p-chlorophenyl moiety (acetal part) is replaced by a phenyl moiety, the $EC_{50}$ value increases to >80 μg/ml. This shows the chloro atom is required for the activity. In an analogous way it can be seen that substitution of the ethyl (C2 and C3) group by a methyl or an allyl group leads to a loss of the activity, evidencing that these groups are required for biological activity. With the aid software, CS Chem3D® Version 4.0 for Windows NT, from CambridgeSoft Corporation, the energy of Compound A1 has been minimized using the MM2 force field. The internal coordinates of all atoms and lone pairs (Lp) are listed in Table 5.

TABLE 5

| Internal coordinates of Compound A1 (bond lengths in ' ngstroms) | | | | | | | |
|---|---|---|---|---|---|---|---|
| Atom | Bond atom | Bond length | Angle atom | First angle | Third atom | Second angle | Angle type |
| C(19) | | | | | | | |
| C(20) | C(19) | 1.400 | | | | | |

TABLE 5-continued

Internal coordinates of Compound A1 (bond lengths in ' ngstroms)

| Atom | Bond atom | Bond length | Angle atom | First angle | Third atom | Second angle | Angle type |
|---|---|---|---|---|---|---|---|
| C(28) | C(19) | 1.400 | C(20) | 118.489 | | | |
| C(22) | C(20) | 1.396 | C(19) | 120.917 | C(28) | 0.079 | Dihedral |
| C(24) | C(22) | 1.396 | C(20) | 120.020 | C(19) | 0.000 | Dihedral |
| C(26) | C(28) | 1.396 | C(19) | 120.887 | C(20) | −0.099 | Dihedral |
| C(30) | C(19) | 1.511 | C(20) | 120.484 | C(28) | 121.017 | Pro-S |
| C(2) | C(30) | 1.537 | C(19) | 114.950 | C(20) | 77.574 | Dihedral |
| C(1) | C(2) | 1.539 | C(30) | 113.272 | C(19) | 65.511 | Dihedral |
| O(3) | C(2) | 1.420 | C(1) | 112.464 | C(30) | 105.600 | Pro-R |
| C(4) | O(3) | 1.411 | C(2) | 112.094 | C(1) | −56.577 | Dihedral |
| C(5) | C(4) | 1.512 | O(3) | 108.311 | C(2) | 67.859 | Dihedral |
| C(7) | C(4) | 1.518 | C(5) | 109.153 | O(3) | 110.004 | Pro-R |
| O(16) | C(5) | 1.415 | C(4) | 107.813 | C(7) | 53.996 | Dihedral |
| C(6) | C(5) | 1.524 | C(4) | 109.912 | O(16) | 111.101 | Pro-S |
| O(8) | C(6) | 1.426 | C(1) | 108.451 | C(5) | 108.926 | Pro-R |
| C(13) | O(8) | 1.419 | C(6) | 114.920 | C(1) | −148.229 | Dihedral |
| C(9) | C(13) | 1.526 | O(8) | 108.224 | C(6) | 174.564 | Dihedral |
| C(18) | O(16) | 1.422 | C(5) | 111.988 | C(4) | −62.011 | Dihedral |
| O(33) | C(1) | 1.427 | C(2) | 105.741 | C(6) | 111.486 | Pro-S |
| C(38) | O(33) | 1.417 | C(1) | 116.052 | C(2) | 169.464 | Dihedral |
| C(34) | C(38) | 1.526 | O(33) | 108.830 | C(1) | −167.938 | Dihedral |
| C(41) | C(18) | 1.517 | O(16) | 108.976 | C(5) | −171.786 | Dihedral |
| O(17) | C(18) | 1.422 | O(16) | 106.317 | C(41) | 112.711 | Pro-R |
| C(42) | C(41) | 1.400 | C(18) | 122.741 | O(16) | −120.460 | Dihedral |
| C(46) | C(41) | 1.400 | C(42) | 118.215 | C(18) | 119.043 | Pro-R |
| C(43) | C(42) | 1.397 | C(41) | 120.960 | C(46) | −0.069 | Dihedral |
| C(44) | C(43) | 1.396 | C(42) | 120.036 | C(41) | −0.108 | Dihedral |
| C(45) | C(46) | 1.396 | C(41) | 121.317 | C(42) | 0.219 | Dihedral |
| Cl(47) | C(44) | 1.724 | C(43) | 120.183 | C(45) | 120.072 | Pro-S |
| H(58) | C(1) | 1.116 | C(2) | 107.183 | C(6) | 108.862 | Pro-R |
| H(59) | C(2) | 1.117 | C(1) | 109.405 | O(3) | 107.291 | Pro-R |
| H(57) | C(4) | 1.116 | O(3) | 109.623 | C(5) | 111.118 | Pro-R |
| H(56) | C(5) | 1.116 | C(4) | 110.302 | C(6) | 108.796 | Pro-S |
| H(52) | C(6) | 1.114 | C(1) | 108.575 | C(5) | 109.954 | Pro-S |
| H(54) | C(7) | 1.114 | C(4) | 110.718 | O(17) | 107.798 | Pro-R |
| H(55) | C(7) | 1.113 | C(4) | 112.030 | O(17) | 109.460 | Pro-S |
| H(10) | C(9) | 1.114 | C(13) | 111.090 | O(8) | 179.396 | Dihedral |
| H(11) | C(9) | 1.115 | C(13) | 110.947 | H(10) | 107.795 | Pro-S |
| H(12) | C(9) | 1.114 | C(13) | 111.116 | H(10) | 107.828 | Pro-R |
| H(14) | C(13) | 1.114 | O(8) | 109.916 | C(6) | 54.950 | Dihedral |
| H(15) | C(13) | 1.111 | O(8) | 110.424 | C(9) | 109.409 | Pro-S |
| H(53) | C(18) | 1.113 | O(16) | 110.960 | O(17) | 110.250 | Pro-R |
| H(21) | C(20) | 1.102 | C(19) | 119.781 | C(22) | 119.301 | Pro-R |
| H(23) | C(22) | 1.102 | C(20) | 120.021 | C(24) | 119.958 | Pro-R |
| H(25) | C(24) | 1.102 | C(22) | 120.191 | C(26) | 120.164 | Pro-R |
| H(27) | C(26) | 1.102 | C(24) | 119.972 | C(28) | 119.985 | Pro-S |
| H(29) | C(28) | 1.102 | C(19) | 119.961 | C(26) | 119.150 | Pro-R |
| H(31) | C(30) | 1.117 | C(2) | 109.382 | C(19) | 107.248 | Pro-S |
| H(32) | C(30) | 1.115 | C(2) | 109.423 | C(19) | 110.067 | Pro-R |
| H(35) | C(34) | 1.114 | C(38) | 110.912 | O(33) | −177.128 | Dihedral |
| H(36) | C(34) | 1.114 | C(38) | 111.236 | H(35) | 107.870 | Pro-S |
| H(37) | C(34) | 1.113 | C(38) | 111.274 | H(35) | 107.511 | Pro-R |
| H(39) | C(38) | 1.113 | O(33) | 109.474 | C(1) | 74.497 | Dihedral |
| H(40) | C(38) | 1.114 | O(33) | 110.053 | C(34) | 109.950 | Pro-S |
| H(51) | C(42) | 1.101 | C(41) | 120.623 | C(43) | 118.417 | Pro-R |
| H(49) | C(43) | 1.102 | C(42) | 119.394 | C(44) | 120.570 | Pro-R |
| H(48) | C(45) | 1.102 | C(44) | 120.814 | C(46) | 119.459 | Pro-R |
| H(50) | C(46) | 1.102 | C(45) | 119.051 | C(41) | 119.631 | Pro-R |
| Lp(60) | O(3) | 0.602 | C(2) | 105.379 | C(4) | 104.222 | Pro-R |
| Lp(61) | O(3) | 0.600 | C(2) | 104.140 | C(4) | 103.574 | Pro-S |
| Lp(62) | O(8) | 0.600 | C(6) | 103.720 | C(13) | 104.700 | Pro-R |
| Lp(63) | O(8) | 0.597 | C(6) | 103.883 | C(13) | 104.472 | Pro-S |
| Lp(64) | O(16) | 0.598 | C(5) | 104.207 | C(18) | 103.670 | Pro-R |
| Lp(65) | O(16) | 0.600 | C(5) | 103.930 | C(18) | 104.822 | Pro-S |
| Lp(66) | O(17) | 0.600 | C(7) | 104.221 | C(18) | 103.758 | Pro-R |
| Lp(67) | O(17) | 0.602 | C(7) | 104.885 | C(18) | 103.727 | Pro-S |
| Lp(68) | O(33) | 0.599 | C(1) | 103.726 | C(38) | 103.806 | Pro-R |
| Lp(69) | O(33) | 0.601 | C(1) | 103.118 | C(38) | 104.600 | Pro-S |

Figure 6:
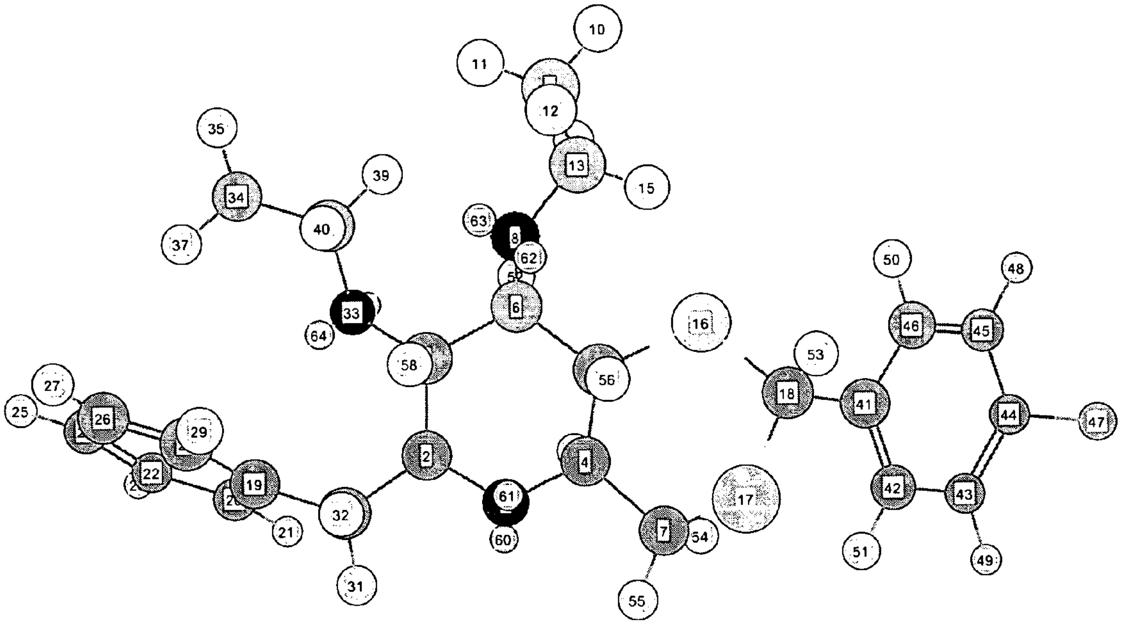
FIG. 6 is a three-dimensional representation of Compound A2.

Without being restricted to any particular theory, as discussed above, it is believed that the activity of Compound A1 is at least partially related to its spatial occupation and three-dimensional configuration. Substitutions of certain moieties in compound A1 which do not alter the internal coordinates by an amount in excess of 10% will not change its spatial occupation and three-dimensional configuration so as to destroy its activity and may actually enhance activity. For example, substitution of sulfur atoms for the oxygen atoms at locations 16 and 17 results in a compound designated Compound A2 (FIG. 6) and the CS Chem3D® software generates the following table of internal coordi¯ nates.

TABLE 6

Internal coordinates of Compound A2 (bond lengths in ' ngstroms)

| Atom | Bond atom | Bond length | Angle atom | First angle | Third atom | Second angle | Angle type |
|---|---|---|---|---|---|---|---|
| C(19) | | | | | | | |
| C(20) | C(19) | 1.400 | | | | | |
| C(28) | C(19) | 1.400 | C(20) | 118.424 | | | |
| C(22) | C(20) | 1.396 | C(19) | 120.987 | C(28) | 0.497 | Dihedral |
| C(24) | C(22) | 1.396 | C(20) | 119.993 | C(19) | −0.137 | Dihedral |
| C(26) | C(28) | 1.396 | C(19) | 120.888 | C(20) | −0.370 | Dihedral |
| C(30) | C(19) | 1.512 | C(20) | 120.460 | C(28) | 121.112 | Pro-S |
| C(2) | C(30) | 1.537 | C(19) | 114.295 | C(20) | 71.031 | Dihedral |
| C(1) | C(2) | 1.531 | C(30) | 113.854 | C(19) | 69.505 | Dihedral |
| O(3) | C(2) | 1.418 | C(1) | 110.860 | C(30) | 106.410 | Pro-R |
| C(4) | O(3) | 1.415 | C(2) | 111.903 | C(1) | −63.680 | Dihedral |
| C(5) | C(4) | 1.531 | O(3) | 108.407 | C(2) | 68.982 | Dihedral |
| C(7) | C(4) | 1.541 | C(5) | 116.631 | O(3) | 108.720 | Pro-R |
| S(16) | C(5) | 1.828 | C(4) | 104.369 | C(7) | 59.299 | Dihedral |
| C(6) | C(5) | 1.540 | C(4) | 112.149 | S(16) | 111.521 | Pro-S |
| O(8) | C(6) | 1.428 | C(1) | 105.702 | C(5) | 110.529 | Pro-R |
| C(13) | O(8) | 1.416 | C(6) | 116.263 | C(1) | −161.576 | Dihedral |
| C(9) | C(13) | 1.527 | O(8) | 108.190 | C(6) | 165.732 | Dihedral |
| C(18) | S(16) | 1.824 | C(5) | 99.519 | C(4) | −73.887 | Dihedral |
| O(33) | C(1) | 1.427 | C(2) | 106.033 | C(6) | 111.688 | Pro-S |
| C(38) | O(33) | 1.417 | C(1) | 116.023 | C(2) | 170.029 | Dihedral |
| C(34) | C(38) | 1.526 | O(33) | 108.681 | C(1) | −167.389 | Dihedral |
| C(41) | C(18) | 1.522 | S(16) | 107.403 | C(5) | 149.188 | Dihedral |
| S(17) | C(18) | 1.823 | S(16) | 115.437 | C(41) | 115.201 | Pro-R |
| C(42) | C(41) | 1.403 | C(18) | 124.027 | S(16) | −119.356 | Dihedral |
| C(46) | C(41) | 1.404 | C(42) | 116.823 | C(18) | 119.145 | Pro-S |
| C(43) | C(42) | 1.397 | C(41) | 121.800 | C(46) | −1.237 | Dihedral |
| C(44) | C(43) | 1.395 | C(42) | 120.102 | C(41) | 0.000 | Dihedral |
| C(45) | C(46) | 1.396 | C(41) | 122.092 | C(42) | 1.739 | Dihedral |
| Cl(47) | C(44) | 1.724 | C(43) | 120.282 | C(45) | 120.376 | Pro-S |
| H(58) | C(1) | 1.116 | C(2) | 106.528 | C(6) | 109.122 | Pro-R |
| H(59) | C(2) | 1.116 | C(1) | 109.601 | O(3) | 108.074 | Pro-R |
| H(57) | C(4) | 1.119 | O(3) | 107.138 | C(5) | 109.344 | Pro-R |
| H(56) | C(5) | 1.116 | C(4) | 110.041 | C(6) | 106.480 | Pro-S |
| H(52) | C(6) | 1.115 | C(1) | 107.272 | C(5) | 110.458 | Pro-S |
| H(54) | C(7) | 1.115 | C(4) | 109.696 | S(17) | 109.311 | Pro-R |
| H(55) | C(7) | 1.115 | C(4) | 110.556 | S(17) | 109.196 | Pro-S |
| H(10) | C(9) | 1.114 | C(13) | 111.082 | O(8) | 178.753 | Dihedral |
| H(11) | C(9) | 1.114 | C(13) | 111.026 | H(10) | 107.808 | Pro-S |
| H(12) | C(9) | 1.115 | C(13) | 111.132 | H(10) | 107.789 | Pro-R |
| H(14) | C(13) | 1.114 | O(8) | 110.164 | C(6) | 45.798 | Dihedral |
| H(15) | C(13) | 1.112 | O(8) | 109.527 | C(9) | 108.577 | Pro-S |
| H(53) | C(18) | 1.119 | S(16) | 107.477 | S(17) | 104.877 | Pro-R |
| H(21) | C(20) | 1.102 | C(19) | 119.841 | C(22) | 119.172 | Pro-R |
| H(23) | C(22) | 1.102 | C(20) | 120.037 | C(24) | 119.970 | Pro-R |
| H(25) | C(24) | 1.102 | C(22) | 120.187 | C(26) | 120.193 | Pro-R |
| H(27) | C(26) | 1.102 | C(24) | 119.929 | C(28) | 119.983 | Pro-S |
| H(29) | C(28) | 1.102 | C(19) | 119.976 | C(26) | 119.133 | Pro-R |
| H(31) | C(30) | 1.117 | C(2) | 109.431 | C(19) | 106.771 | Pro-S |
| H(32) | C(30) | 1.114 | C(2) | 109.685 | C(19) | 110.712 | Pro-R |
| H(35) | C(34) | 1.114 | C(38) | 111.008 | O(33) | −177.595 | Dihedral |
| H(36) | C(34) | 1.114 | C(38) | 111.215 | H(35) | 107.941 | Pro-S |
| H(37) | C(34) | 1.113 | C(38) | 111.142 | H(35) | 107.497 | Pro-R |
| H(39) | C(38) | 1.114 | O(33) | 109.530 | C(1) | 74.595 | Dihedral |
| H(40) | C(38) | 1.114 | O(33) | 110.007 | C(34) | 109.677 | Pro-S |
| H(51) | C(42) | 1.100 | C(41) | 121.551 | C(43) | 116.649 | Pro-S |
| H(49) | C(43) | 1.103 | C(42) | 119.420 | C(44) | 120.478 | Pro-R |
| H(48) | C(45) | 1.102 | C(44) | 120.622 | C(46) | 119.558 | Pro-S |
| H(50) | C(46) | 1.103 | C(45) | 118.124 | C(41) | 119.783 | Pro-R |
| Lp(60) | O(3) | 0.601 | C(2) | 104.847 | C(4) | 104.264 | Pro-R |
| Lp(61) | O(3) | 0.600 | C(2) | 104.338 | C(4) | 103.749 | Pro-S |
| Lp(62) | O(8) | 0.600 | C(6) | 103.356 | C(13) | 104.579 | Pro-R |
| Lp(63) | O(8) | 0.596 | C(6) | 103.755 | C(13) | 103.945 | Pro-S |

TABLE 6-continued

| Internal coordinates of Compound A2 (bond lengths in ' ngstroms) | | | | | | | |
|---|---|---|---|---|---|---|---|
| Atom | Bond atom | Bond length | Angle atom | First angle | Third atom | Second angle | Angle type |
| Lp(64) | O(33) | 0.599 | C(1) | 103.674 | C(38) | 103.749 | Pro-R |
| Lp(65) | O(33) | 0.601 | C(1) | 103.158 | C(38) | 104.689 | Pro-S |

Sulfur has a larger Van der Waals radius (1.85')compared to oxygen (1.4') and nitrogen (1.45'). The effect of this substitution on the overall spatial occupation of the molecule can be compared by examining, for example, the distance between H(25) and Cl(47) in the two molecules Compound A1 and Compound A2. The values are depicted in Table 7.

TABLE 7

| Distance comparison with sulfur substitution | | |
|---|---|---|
| | Compound A1 | S analog of Compound A1 (Compound A2) |
| H(25)-Cl(45) distance in | 16.445 | 15.917 |

In a similar fashion, it can be shown that substituting nitrogen and/or sulfur for oxygen in the positions $X_1$, $X_2$, and $X_3$ of Formula A and substituting nitrogen and/or sulfur for oxygen in the positions $Y_1$ and $Y_2$ and substituting fluorine and bromine for chlorine in the Z position of Compound A1 does not change the total spatial occupation of Compound A1 by more than 10%.

CONCLUSION

Compounds of Formula A and, in particular, Compound A1, have a very high potency against HSV. The experiments not only revealed a similar activity against HSV-1 as acyclovir, but even a superior effect against HSV-2. An additional important advantage is its selectivity index >3333. Compound A1 did not show activity against other viruses tested, nor against bacteria and fungi, evidence that Compound A1 is highly selective. This compound is especially interesting because it is a non-nucleoside that may have a different target in the viral replication cycle and thus be still active against nucleoside-resistant HSV infections.

Although the invention has been described with respect to a preferred embodiment thereof, it is to be also understood that it is not to be so limited since changes and modifications can be made therein which are within the full intended scope of this invention as defined by the appended claims.

We claim:

1. A method of treating an infection caused by herpesvirinae in a patient in need thereof comprising administering to said patient an effective amount of at least one compound according to the chemical structure

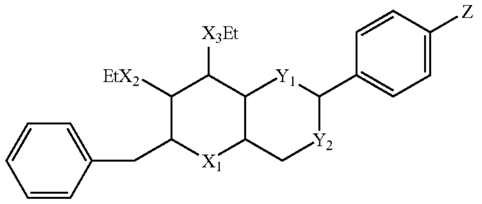

wherein $X_1$, $X_2$, and $X_3$ are;

wherein $Y_1$ and $Y_2$ are; and wherein Z is selected from the group consisting of F, Cl, and Br.

2. A method as defined in claim 1, wherein the patient is administered an effective amount of at least one pharmaceutically acceptable salt of the compounds of claim 1.

3. A method as defined in claim 1, wherein said compounds have substantially identical spatial occupation, physiochemical and electrochemical properties as the compounds of claim 1.

4. A method of treating an infection caused by herpesvirinae in a patient in need thereof comprising administering to said patient an effective amount of a compound of the chemical structure

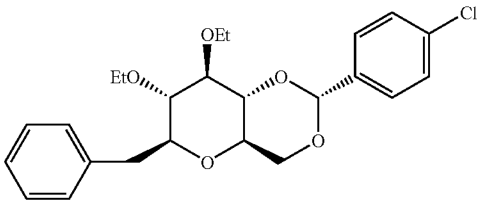

or a pharmaceutically acceptable salt thereof.

5. A method as defined in claim 1 comprising the administration of an effective amount of a compound of claim 1 and a pharmaceutically acceptable carrier.

6. A method of treating an infection caused by herpesvirinae in a patient in need thereof comprising administering to said patient an effective amount of at least one compound having the three-dimensional structure characterized by the atomic structure coordinates of Table 5, said compound having less than a 10% difference in the internal coordinates after minimalization with the MM2 force field.

7. A method according to claim 1, wherein the infection is caused by HSV-1 or HSV-2.

* * * * *